United States Patent
Clement et al.

(10) Patent No.: US 11,744,805 B2
(45) Date of Patent: Sep. 5, 2023

(54) METHODS FOR VALIDATING AN APPARATUS FOR PRODUCING NANOPARTICLES

(71) Applicant: leon-nanodrugs GmbH, Munich (DE)

(72) Inventors: Pascale Clement, Munich (DE); Beatriz López-Sánchez, Munich (DE)

(73) Assignee: leon-nanodrugs GmbH, Munich (DE)

( * ) Notice: Subject to any disclaimer, the term of this patent is extended or adjusted under 35 U.S.C. 154(b) by 0 days.

(21) Appl. No.: 17/962,635

(22) Filed: Oct. 10, 2022

(65) Prior Publication Data
US 2023/0113636 A1 Apr. 13, 2023

(30) Foreign Application Priority Data
Oct. 11, 2021 (EP) .................................. 21201916

(51) Int. Cl.
A61K 9/51 (2006.01)
B01F 25/23 (2022.01)
B82Y 40/00 (2011.01)
A61K 45/06 (2006.01)
B82Y 5/00 (2011.01)

(52) U.S. Cl.
CPC .......... *A61K 9/5192* (2013.01); *A61K 9/5146* (2013.01); *A61K 9/5161* (2013.01); *A61K 45/06* (2013.01); *B01F 25/23* (2022.01); *B82Y 40/00* (2013.01); *B82Y 5/00* (2013.01)

(58) Field of Classification Search
CPC .. A61K 9/5192; A61K 9/5146; A61K 9/5161; A61K 45/06; B01F 25/23; B82Y 40/00; B82Y 5/00
See application file for complete search history.

(56) References Cited

U.S. PATENT DOCUMENTS

| | | | |
|---|---|---|---|
| 11,395,805 B2 * | 7/2022 | Mao | A61K 9/5192 |
| 2004/0213858 A1 * | 10/2004 | Franceschetti | B01F 33/053 424/724 |
| 2005/0196457 A1 * | 9/2005 | Lyons | A61P 25/18 424/489 |
| 2007/0098757 A1 * | 5/2007 | Klee | A61P 43/00 977/900 |
| 2009/0169637 A1 * | 7/2009 | Makino | A61P 31/04 424/499 |
| 2012/0114759 A1 * | 5/2012 | Green | A61K 9/19 977/773 |
| 2012/0189698 A1 * | 7/2012 | Lopez-Belmonte Encina | A61K 9/5153 977/773 |
| 2013/0122058 A1 * | 5/2013 | Chow | A61K 9/5192 977/773 |
| 2014/0113137 A1 * | 4/2014 | Podobinski | C08F 6/12 428/402 |
| 2015/0064116 A1 * | 3/2015 | Mohapatra | A61K 49/1863 424/174.1 |
| 2015/0273440 A1 * | 10/2015 | Furudate | B01J 23/22 502/309 |
| 2020/0101023 A1 * | 4/2020 | Mao | A61K 47/6455 |
| 2020/0397696 A1 * | 12/2020 | Panagiotou | B01F 35/92 |
| 2021/0208138 A1 * | 7/2021 | Aburaya | G01N 33/54387 |
| 2021/0378980 A1 * | 12/2021 | Horhota | A61K 9/19 |
| 2022/0175687 A1 * | 6/2022 | Suk | A61K 9/5123 |

FOREIGN PATENT DOCUMENTS

| | | |
|---|---|---|
| EP | 1165224 B1 | 9/2002 |
| EP | 2395978 B1 | 5/2015 |
| WO | 200134113 A2 | 5/2001 |

OTHER PUBLICATIONS

Extended European Search Report for Application No. 21201916.0, dated Mar. 24, 2022, 7 pages.

* cited by examiner

*Primary Examiner* — Nathaniel T Woodward
*Assistant Examiner* — Philip L Cotey
(74) *Attorney, Agent, or Firm* — Lippes Mathias LLP

(57) ABSTRACT

The invention provides a method for validating the functioning of an apparatus with a static mixing device for mixing two liquid streams for producing nanoparticles. The static mixing device may be a jet impingement reactor. The method is based on the use of PLA, PLG or PLGA for producing polymeric nanoparticles with highly reproducible particle sizes. The invention further provides kits and liquid compositions for carrying out the method.

17 Claims, No Drawings

METHODS FOR VALIDATING AN APPARATUS FOR PRODUCING NANOPARTICLES

This application claims the benefit of European Application No. 21201916.0, filed Oct. 11, 2021, the disclosure of which is herein incorporated by reference.

BACKGROUND

Nanoparticles are increasingly used as drug delivery vehicles, as they introduce various pharmaceutical benefits, such as protection of the therapeutic agent from degradation, improved pharmacokinetics, increased solubility and bioavailability, reduced toxicity, decreased immunogenicity, control over the release rate, targeted delivery, and increased therapeutic efficacy.

A particularly efficient method for nanoparticle manufacturing involves nanoparticle synthesis by solvent/nonsolvent nanoprecipitation. In nanoprecipitation, the nanoparticle components are dissolved in a solvent, which is then impinged as a liquid jet into a mixing chamber in which it collides with a second liquid jet that contains a nonsolvent. The collision of the solvent and the nonsolvent jets induces the precipitation of the dissolved components as nanoparticles. Microjet reactor technologies can be used for automated, continuous nanoparticle synthesis by solvent/nonsolvent precipitation methods. Microjet reactor technology creates a turbulent mixing zone of solvent and nonsolvent and is therefore particularly suitable for the precipitation of particles in the nanometer range. EP 2395978 B1 and EP 1165224 B1 describe solvent/nonsolvent precipitation of nanoparticles by using microjet reactors.

Importantly, the physicochemical characteristics of nanoparticles are particularly sensitive to manufacturing conditions. Therefore, precise and reproducible control of the manufacturing process is necessary to ensure consistent particle characteristics. A wide range of parameters, including the solvent/nonsolvent mixing dynamics, temperature, pH, nanoparticle composition, shear forces, jet velocity, jet pressure, and solvent/nonsolvent volume ratio affect the self-assembly process and thus the physicochemical and pharmacological properties of the nanoparticles. In some instances, laborious processes such as sonication, homogenization, or membrane extrusion, are required to ensure that the produced nanoparticles fulfil the desired characteristics.

Thus, it is critical to provide a practical and reliable validation method for verifying the accuracy of the parameters of the manufacturing reaction. One of the validation methods used to date consists in precipitating hydroxypropyl methylcellulose phthalate from a solvent stream collided with an aqueous stream, and then evaluating the nanoparticles formed by the process. However, the size of the nanoparticles generated by this method is not sensitive enough to the reaction conditions. In particular the size of the particles does not depend on volume ratio of the ethanolic stream and the water stream injected to the reactor. A further validation method was recently proposed in which a solvent stream comprising itraconazole is collided with an aqueous stream at some desired conditions, and then the size of the obtained itraconazole-containing nanoparticles is measured and compared to the expected nanoparticle size for said conditions. The size of precipitated itraconazole nanoparticles is sensitive enough to modest alterations in reaction conditions. However, the use of itraconazole is problematic, as it leads to cross-contamination of products prepared in the validated microreactor.

Thus, it is not possible to test experimentally in a fast and easy-to-perform precipitation procedure whether the target process parameters correspond to the actual process parameters. It would be desirable, for example, if the volume ratio of solvent stream to antisolvent stream could be experimentally checked in a simple and fast procedure, without using cross-contaminating substances.

Thus, there is a need for a suitable and improved method for validating reactors. The present disclosure provides a validation method for the operability of a system for the production of nanoparticles that leads to reliable results, without the use of cross-contaminating substances.

SUMMARY OF THE INVENTION

In a first aspect, the present invention provides a method for validating the functioning of an apparatus for producing nanoparticles, wherein the apparatus comprises a static mixing device for mixing two liquid streams having a first fluid inlet, a second fluid inlet, a mixing zone and a fluid outlet. The method generally comprises the steps of (a) providing a first specimen of said apparatus; (b) providing a first stream of a first liquid composition, wherein the first liquid composition comprises an organic solution of a polymer selected from PLA, PGA, PLGA and combinations thereof; (c) providing a second stream of a second liquid composition, wherein the second liquid composition is an aqueous solution; (d) simultaneously injecting the first stream at a first flow rate through the first fluid inlet, and the second stream at a second flow rate through the second fluid inlet into the static mixing device of a first specimen of the apparatus such as to allow the first liquid composition and the second liquid composition to mix in the mixing zone and to form polymer nanoparticles; (e) measuring the average particle size of the nanoparticles obtained in step (d); and subsequently (f) repeating steps (a) to (e) using essentially the same liquid compositions and the same flow rates but a second specimen of the apparatus; (g) determining whether the difference between the average particle size obtained when step (e) was repeated and the average particle size obtained when step (e) was performed for the first time is larger than a predefined tolerance value; and (h) if said difference is not larger than the predefined tolerance value, using the second specimen of the apparatus for preparing nanoparticles by mixing two liquid streams that do not comprise the first liquid composition.

The method may be used to validate the proper functioning of an apparatus after it has been disassembled and reassembled, e.g. for cleaning purposes, i.e. by comparing nanoparticle sizes generated by the same apparatus using the same liquid streams before and after cleaning and reassembly; or it may be used for ensuring the proper functioning of e.g. a new apparatus of the same type and setup as another apparatus by comparing the nanoparticle sizes obtained by the two respective apparatuses using the same liquid streams. In other words, the apparatus used for the first series of steps (a) to (e) may be the same or different from the apparatus used for the repetition of these steps according to step (f).

Preferably, the apparatus comprises a jet impingement reactor as static mixing device.

In a further aspect, the invention provides a kit useful for conducting the method of the invention. The kit comprises a first kit component comprising an amount of a first liquid composition comprising an organic solution of a polymer selected from PLA, PGA, PLGA and combinations thereof and a second kit component comprising an amount of a second liquid composition representing an aqueous solution.

In further aspects, the invention relates to the use of such kit or of an organic solution of a polymer selected from PLA, PGA, PLGA and combinations thereof for validating the functioning of an apparatus for producing nanoparticles, wherein the apparatus comprises a static mixing device as described herein.

One particular advantage of the invention is that it allows the validation of the functioning of apparatuses for producing nanoparticles based on static mixing of two liquid streams without using or introducing biologically active materials which could potentially cause undesirable cross-contamination of a product subsequently produced on a validated apparatus.

DETAILED DESCRIPTION OF THE INVENTION

In one aspect, the present invention provides a method for validating the functioning of an apparatus for producing nanoparticles, wherein the apparatus comprises a static mixing device for mixing two liquid streams having a first fluid inlet, a second fluid inlet, a mixing zone and a fluid outlet. The method generally comprises the steps of (a) providing a first specimen of said apparatus; (b) providing a first stream of a first liquid composition, wherein the first liquid composition comprises an organic solution of a polymer selected from PLA, PGA, PLGA and combinations thereof; (c) providing a second stream of a second liquid composition, wherein the second liquid composition is an aqueous solution; (d) simultaneously injecting the first stream at a first flow rate through the first fluid inlet, and the second stream at a second flow rate through the second fluid inlet into the static mixing device of a first specimen of the apparatus such as to allow the first liquid composition and the second liquid composition to mix in the mixing zone and to form polymer nanoparticles; (e) measuring the average particle size of the nanoparticles obtained in step (d); and subsequently (f) repeating steps (a) to (e) using essentially the same liquid compositions and the same flow rates but a second specimen of the apparatus; (g) determining whether the difference between the average particle size obtained when step (e) was repeated and the average particle size obtained when step (e) was performed for the first time is larger than a predefined tolerance value; and (h) if said difference is not larger than the predefined tolerance value, using the second specimen of the apparatus for preparing nanoparticles by mixing two liquid streams that do not comprise the first liquid composition.

The inventors have unexpectedly found that biocompatible and biologically inert materials, i.e. polymers selected from PLA, PGA, PLGA and combinations of these, may be used to validate the proper functioning of an apparatus for producing nanoparticles, which is in contrast to the prior art that relies on using small molecules for generating nanoparticles for validation purposes, such as certain drug substances which bring about some risk of cross-contaminating products subsequently manufactured using a validated apparatus. The invention is also based on the discovery that PLA, PGA, PLGA may be used to manufacture nanoparticles, in particular drug-free nanoparticles, whose particle size directly results from the apparatus configuration and the process parameters used. In other words, the PLA, PGA, and/or PLGA nanoparticle sizes produced on the type of apparatus described herein are sufficiently predictable to allow the use of these polymers for validating such apparatus. Vice versa, if an apparatus is e.g. disassembled for cleaning purposed and then not carefully reassembled such as to achieve precisely the previous configuration (e.g. with respect to the proper alignment of the nozzle in case of an apparatus comprising a jet impingement reactor), this would lead to a difference in the particle size of the polymeric nanoparticles produced in the validation method and thus be detected as improper functioning of the apparatus after reassembly.

In the context of the invention, validating or validation means ensuring or verifying that an apparatus functions properly, which implies that it has been assembled correctly such as to have exactly the same configuration as intended, e.g. with respect to nozzle sizes, nozzle alignment and the like; and that the intended process parameters are actually achieved, e.g. flow rates or pressures. Such process parameters would also be affected by other components of the apparatus, such as pumps and valves. It is noted that validation may also have very specific regulatory meanings in the pharmaceutical industry which are not meant to be implied in the context of the invention.

Nanoparticles, as used herein, are particles having an average particle size of less than about 1,000 nm. Preferably, the invention uses nanoparticles having an average particle size in the range of about 10 nm to about 500 nm. In this context, the average particle size is preferably expressed as the z-average particle size as measured by laser diffraction or dynamic light scattering. It is not crucial exactly which method or instrument is used for determining the average particle size as long as the same method and the same or a comparable instrument are used when comparing the particle sizes in step (g) of the method according to the invention. Unless the context dictates otherwise, a reference to a particle size or to particle sizes should be understood as a reference to the average particle size(s).

A static mixing device, as used herein, is any mixer or mixing device that does not rely on moving parts for performing a mixing process. An example of a very simple static mixing device is a T-piece.

PLA means poly(lactic acid), also referred to polylactide; PLG means poly(glycolic acid), or polyglycolide; and PLGA is used to refer to the copolymer poly(lactic-co-glycolic acid) or polylactide-co-glycolide.

An organic solution of a polymer, as used herein, refers to a liquid composition in which the polymer exists in the dissolved state, and wherein the liquid constituent(s) are predominantly organic.

Preferably, the first specimen and the second specimen of the apparatus have essentially the same design and configuration. The first specimen may or may not be identical to the second specimen. The identical second specimen preferably also has the same configuration and is used under the same conditions and with the same process parameters or settings.

Alternatively, the method may be used for validating the functioning of a second specimen of an apparatus which is neither identical to the first specimen nor has the same design or configuration of the first specimen, provided that a specific relationship or correlation function has been established with respect to the average particle sizes obtained when using the first or the second specimen, respectively.

In the context of the invention, the configuration of an apparatus refers to the selection of options with respect to hardware components. For example, if the static mixing device is a jet impingement reactor whose inlets have nozzles, the same configuration means amongst others that the same nozzles or nozzle dimensions are used, and the nozzles have the same orientation and the same distance to each other.

In one of the preferred embodiments, the second specimen of the apparatus is identical with the first specimen, and the apparatus is, between steps (e) when performed for the first time and step (f) disassembled and reassembled, and/or cleaned, and/or used for preparing nanoparticles comprising a biologically active ingredient. Preferably, the second specimen also has the same configuration as the first specimen.

For example, the apparatus when used in a specific configuration and with specific process parameters may lead to a specific average particle size of PLA, PGA, and/or PLGA nanoparticles as established by performing method steps (a) to (e). In a typical scenario, this apparatus (i.e. the same specimen) may now be used for preparing a product of interest, such as nanoparticles comprising a biologically or pharmaceutically active ingredient. Before the same apparatus can be used for preparing another (i.e. a different) product of interest, it would normally have to be disassembled, cleaned in order to avoid cross-contamination, and then reassembled. To ensure that in particular the reassembly of the apparatus has been performed correctly and with the required degree of precision, method steps (f) to (h) may now be performed in order to verify that the apparatus is now again in the desired configuration required for its proper functioning, i.e. its functioning in the desired or predetermined manner.

Preferably, in the context of this embodiment, the apparatus (i.e. the specimen) is not disassembled and reassembled, and/or used for preparing nanoparticles comprising a biologically active ingredient between steps (g) and (h). In other words, it is preferred that whenever the apparatus is disassembled and reassembled or used for preparing a product of interest that is not inert but comprises a biologically active ingredient, it should be re-validated by subsequently performing steps (f) to (h) to ensure the proper configuration and functioning of the apparatus.

In an alternative preferred embodiment, the method is performed with a second specimen of the apparatus that is not identical with the first specimen. Preferably, however, the second specimen is of the same type and desired configuration as the first specimen. In other words, an apparatus specimen such as a newly manufactured specimen is validated by comparing the nanoparticles produced with it according to the invention to those previously produced by another reactor of the same type and configuration such as to ensure that the second specimen was properly manufactured, assembled and/or configured.

As mentioned, the static mixing device of the apparatus may in principle be any mixer or mixing device that does not have any moving parts or at least does not rely on moving parts for achieving the mixing effect. In one of the preferred embodiments, the static mixing device is or comprises a T-piece mixer, a Y-piece mixer, a vortex mixer, a baffle-based static mixer, a microfluidic mixing device, or a jet impingement reactor.

Particularly preferred is an apparatus in which the static mixing device is a jet impingement reactor. Typically, the jet impingement reactor comprises a reaction chamber (or reactor chamber, or mixing chamber) defined by a reactor wall which represents the mixing zone, i.e. the zone where the two liquid streams meet and mix such as to form polymeric nanoparticles, as featured in step (d) of the method of the invention. Preferably, the two liquid streams meet in a central area of the reaction chamber. It is also preferred that step (d) is performed in such a way that turbulent mixing of the two liquid streams occurs.

In a further preferred embodiment, the jet impingement reactor is characterised in that the first and the second fluid inlet are arranged at opposite positions of the reactor wall on a first central axis of the reaction chamber such as to point at one another, and wherein each of the first and the second fluid inlet comprises a nozzle. Moreover, the fluid outlet is preferably arranged at a position of the reactor wall that is located on a second central axis of said chamber, the second central axis being perpendicular to the first central axis.

Further options and preferences relating to jet impingement reactors that are useful for carrying out the present invention are described in the co-pending patent application no. EP21192535.9, which is incorporated herein by reference.

As mentioned, a particular advantage of the invention is that it enables the validation of a new, or newly (re-)assembled apparatus without the use of reference materials that are biologically or pharmacologically active and that require specific precautions in order to avoid the cross-contamination of products manufactured with the respective apparatus after it has been validated. This advantage is based on the discovery that the polymers PLA, PGA and PLGA show a behaviour that allows their use as reference materials for the apparatuses described herein. It is noted that these polymers are not only available in pharmaceutical grades, but they are also biologically or pharmacologically substantially inert in that they are approved by major regulatory agencies such as the FDA as pharmaceutical excipients for various uses including parenteral use.

In order to make effective use of this advantage of the invention, it is generally preferred that the method is conducted in the absence of compounds or materials that are biologically or pharmacologically active. In particular, it is preferred that the first liquid composition and the second liquid composition are essentially free of any biologically active ingredient. As used herein, biologically active means that a compound or material would, in the amounts in which they are typically used in pharmaceutical formulations or processing, in a person exposed to it would lead to a pharmacological or toxic effect due to which such compound or material would not normally be safe to use as an excipient. This preference is generally applicable to, and combinable with, all other preferred embodiments disclosed herein.

As mentioned, the first liquid composition is or comprises an organic solution of a polymer selected from PLA, PGA, PLGA and any combinations thereof. In one of the preferred embodiments, the polymer is a PLGA. Various pharmaceutical grades of PLGA are available and may be useful for carrying out the invention. These grades may, for example, differ in the ratio of lactide versus glycolide units, or in the average molecular weight. One example of a useful PLGA polymer is a PLGA having about 75% lactide units and about 25% glycolide units, and an average molecular weight of about 20 kDa. Preferably, the PLGA has an acidic end group, e.g. a carboxyl end group, and/or is unmodified. Other grades of PLGA may also be used, as well as combinations or more than one PLGA, or combinations of a PLGA with a PLA or PGA.

In one embodiment, the first liquid composition comprises only one polymer, or only one polymer grade. For example, the first liquid composition may comprise only one grade of PLGA and otherwise be free of any other polymer.

Moreover, the first liquid composition may, according to another preferred embodiment, also be essentially free of any other solutes.

With respect to the liquid constituent(s) of the first liquid composition, which function as a solvent for the polymer, these may comprise a single organic solvent or a mixture of organic solvents. Water may also be present in the first liquid composition, but only to the extent that the amount of water is small relative to the amount of the organic solvent or solvents.

In one of the preferred embodiments, the first liquid composition is water-miscible, and thus miscible with the second liquid composition which is aqueous. This would imply that the organic solvent used in the composition, or if a combination of organic solvents is used, at least the quantitatively dominant organic solvent is water-miscible. Examples of water-miscible solvents that may be used include, without limitation, acetone, ethanol, methanol, and dimethyl sulfoxide (DMSO). In one embodiment, the second liquid composition comprises acetone as the sole or dominant organic solvent. As used herein, dominant means that the relevant properties of the respective solvent prevail over those of any other solvents that may be present in the first liquid composition.

As discussed above, it is particularly preferred that the first liquid composition is essentially free of any biologically active agent.

An example of a particularly useful first liquid composition for carrying out the invention is, without limitation, a solution of PLGA in acetone. Also preferred is a first liquid composition consisting of a solution of a PLGA having a lactide:glycolide ratio of 75:25, an acidic end group, and a mean molecular weight of approximately 20 kDa in acetone.

The amount or concentration of the polymer, or in the present case of the PLGA, in the first liquid composition may be selected in view of the polymer grade that is used. In the case of PLGA, and in particular if a PLGA having a lactide:glycolide ratio of 75:25, an acidic end group, and a mean molecular weight of approximately 20 kDa in acetone is used, a polymer concentration in the range from about 10 mg/mL to about 100 mg/mL is preferred. Also preferred are concentrations in the range from about 20 mg/mL to about 80 mg/mL, or in the range from about 20 mg/mL to about 40 mg/mL, such as about 20 mg/mL, 25 mg/mL, 30 mg/mL, 35 mg/mL, 40 mg/mL 45 mg/mL, or about 50 mg/mL.

According to a further preferred embodiment, the second liquid composition which is aqueous in nature represents an aqueous solution of a stabiliser. The stabiliser may be any compound, material or mixture of compounds that is capable of stabilising nanoparticles, in particular against agglomeration. Potentially suitable stabilisers are generally known to a person skilled in the art. Typically, stabilisers are surfactants or water-soluble polymers.

In one of the preferred embodiments, the second liquid composition comprises a surfactant. Potentially suitable surfactants that are capable of stabilising PLA-, PGA-, and in particular PLGA nanoparticles may represent non-ionic, anionic, cationic, zwitterionic or polyelectrolyte surfactants. In a specific preferred embodiment, the surfactant used in the second liquid composition is a non-ionic surfactant. According to a further preferred embodiment, the non-ionic surfactant is selected from polysorbates and poloxamers. Also preferred are polysorbate and poloxamer grades that are approved as excipients in drug products for parenteral use, for example polysorbate 20, polysorbate 80, or poloxamer 144.

In one specific embodiment, the second liquid composition comprises polysorbate 20 at a concentration in the range from about 0.1 wt. % to about 2 wt. %. In a further embodiment, it consists of an aqueous solution of polysorbate 20 having a polymer concentration in the range from about 0.1 wt. % to about 2 wt. %, or of about 0.5 wt. %, or about 1 wt. %, respectively.

Optionally, the second liquid composition further comprises a pH-regulating agent such as an acid, a base, or a buffer salt or a buffer. Optionally, an amount of a water-miscible organic solvent is present, provided that the amount is small relative to the amount of water comprises in the second liquid composition. As discussed above, it is preferred that the second liquid composition is essentially free of any biologically active agent. Again, it is also preferred that both the first and the second liquid composition is essentially free of any biologically active agent.

In one specific embodiment, the first liquid composition consists of a solution of a PLGA having a lactide:glycolide ratio of 75:25, an acidic end group, and a mean molecular weight of approximately 20 kDa in acetone having a polymer concentration in the range from about 10 mg/mL to about 100 mg/mL, and the second liquid composition consists of an aqueous solution of polysorbate 20 having a polymer concentration in the range from about 0.1 wt. % to about 2 wt. %. In another specific embodiment, the first liquid composition consists of a solution of a PLGA having a lactide:glycolide ratio of 75:25, an acidic end group, and a mean molecular weight of approximately 20 kDa in acetone having a polymer concentration in the range from about 10 mg/mL to about 50 mg/mL, and the second liquid composition consists of an aqueous solution of polysorbate 20 having a polymer concentration in the range from about 0.1 wt. % to about 1 wt. %. As described below, such particularly useful first and second liquid compositions may also be combined in a kit of parts, which relates to a further aspect of the invention.

As mentioned, the inventors have found that PLA, PGA and PLGA are surprisingly useful for producing nanoparticles having highly reproducible particle sizes such as to enable their use in validating or verifying the proper configuration or functioning of an apparatus with a static mixing device. Obtaining the average particle size of the nanoparticles produced with a preselected apparatus configuration and preselected process parameters—in particular flow rates—by performing steps (a) to (e) for the first time and then repeating these steps subsequent to e.g. the disassembly, cleaning and reassembly of the apparatus in order to obtain another average particle size which is compared to the first average particle size allows the determination of whether or not the apparatus still has the same desired configuration and functions in the same manner as before disassembly. This determination, according to steps (g) and (h), involves a comparison of the difference between the first and the second average particle size to a predefined tolerance value. Such predefined tolerance value, which is a type of acceptance criterion, should be selected with an eye on the criticality of the average particle size for the quality and performance of the product that is intended to be manufactured next with the validated apparatus. If the average particle size is a highly critical product property, the predefined tolerance value should be low, such as 10% or even 5% of the value of the average particle size as measured in step (e) when this step is performed for the first time. This would mean that if, for example, during the first series of steps (a) to (e) an average particle size (e.g. a z-average) of 100 nm was obtained, the repetition of steps (a) to (e) after disassembly, cleaning and reassembly of the apparatus should lead to nanoparticles having an average particle size in the range from 90 nm to 110 nm, or from 95 nm to 105 nm, respectively. If a particle size within such range is obtained, the apparatus may be used for preparing a product of interest, i.e. by mixing two liquid streams neither of which comprises the first liquid composition, as defined in step (h).

For many other products, a larger tolerance value may be preselected, such as 30%, 25%, or 20%, or 15%, wherein the percentages have the same basis, preferably the value of the average particle size as measured in step (e) when performing said step for the first time. As used herein, the expression "for the first time" should be understood as referring to the first series of steps (a) to (e) in order to obtain a reference value of the average particle size for comparison with a subsequently obtained average particle size measured in step (e) when steps (a) to (e) are repeated for validation purposes. In other words, the expression "for the first time" does not require that steps (a) to (e) have never been performed on the apparatus previously.

In one of the preferred embodiments, the predefined tolerance value is 20%, or 15%, or 10%, or 5% of the value of the average particle size as measured in step (e) when performing said step for the first time, respectively.

The average particle size as determined using dynamic light scattering is according to the presently disclosed method as the only, or primary parameter for determining reproducibility and validation the functioning of an apparatus for producing nanoparticles, however optionally, other parameters may also be considered. For example, polydispersity index (PDI) which is a dimensionless estimate of the width of the particle size distribution, scaled from 0 to 1 may also be, in addition to average particle size, taken into consideration. In an optional embodiment, a polydispersity index of ≤0.25 may be used as a further tolerance value for a validation method as described herein.

According to a further aspect, the invention provides a kit for validating the functioning of an apparatus for producing nanoparticles, wherein said apparatus comprises a static mixing device for mixing two liquid streams, said static mixing device comprising a first fluid inlet, a second fluid inlet, a mixing zone and a fluid outlet, wherein the kit comprises a first kit component comprising an amount of the first liquid composition as defined herein; and a second kit component comprising an amount of the second liquid composition as defined herein.

Such kit is particularly useful for routine validation of the respective apparatuses, especially when working with an apparatus whose static mixing device is a jet impingement reactor, such as a reactor having a reaction chamber defined by a reactor wall, wherein the reaction chamber represents the mixing zone; and wherein the first and the second fluid inlet are arranged at opposite positions of the reactor wall on a first central axis of the reaction chamber such as to point at one another, and wherein each of the first and the second fluid inlet comprises a nozzle; and wherein the fluid outlet is arranged at a position of the reactor wall that is located on a second central axis of said chamber, the second central axis being perpendicular to the first central axis.

With respect to the first liquid composition comprised in the kit, the same options and preferences apply that have been described above in the context of the method of the invention. Similarly, the previously disclosed options and preference relating to the second liquid composition also apply to the second kit component. For example, the kit of the invention may comprise a first kit component comprising a container holding an amount of a solution of PLGA in acetone and a second kit component comprising a container holding an amount of an aqueous solution of a polysorbate, such as polysorbate 20. In one embodiment, each container comprises the amount of liquid required for performing the method of the invention once.

In one embodiment, the kit further comprises instructions for use in the validation of the functioning of an apparatus for producing nanoparticles, in particular an apparatus whose static mixing device is a jet impingement reactor, using said first and second kit components, and wherein the instructions for use describe or comprise the method of validation as described in the present disclosure.

According to a yet further aspect, the invention relates to the use of the kit, or a kit when used as described above, or relates to the use of the first liquid composition and/or the second liquid composition as defined in any one of the embodiments disclosed herein for validating the functioning of an apparatus for producing nanoparticles, wherein said apparatus comprises a static mixing device for mixing two liquid streams, said static mixing device comprising a first fluid inlet, a second fluid inlet, a mixing zone and a fluid outlet. Such uses may be for validating the functioning of an apparatus for producing nanoparticles in accordance with any of the methods as described herein. Again, the use is preferably directed to the validation of apparatuses in which the static mixing device is represented by a jet impingement reactor as described above.

Further options, preferences and embodiments of the invention will become apparent on the basis of the following examples and the patent claims.

EXAMPLES

Example 1

The experiments of this example illustrate the unexpected degree of repeatability of the average particle size of PLGA nanoparticles prepared by jet impingement on which the present invention is based. An apparatus comprising a jet impingement reactor according to EP1165224 was used at room temperature to repeatedly produce PLGA nanoparticles and determine their average particle size (as z-average) by dynamic light scattering. A solution of a PLGA having a lactide:glycolide ratio of 75:25, an acidic end group, and a mean molecular weight of approximately 20 kDa, in acetone having a polymer concentration of 50 mg/mL was used as a first liquid composition, and a solution of polysorbate 20 in water having a surfactant concentration of 1 wt. % was used as the second liquid composition according to the invention. The PLGA solution was injected into the reactor though an inlet having a pinhole nozzle with a diameter of 200 μm, whereas the second inlet through which the aqueous surfactant solution was injected had a pinhole diameter of 300 μm. The surfactant solution was injected into the reactor at a 10 times higher flow rate than the PLGA solution. The mixing of the two liquids lead to the formation of a PLGA nanoparticle dispersion which was discharged from the reactor through an outlet and collected for particle size measurement.

In three series of experiments, the total flow rate (sum of both flow rates) was varied and the resulting average particle size was determined (see table 1). The polydispersity index was in all cases about 0.2, indicating sufficiently monodisperse particle size distributions.

In result, it was found that—within the tested range—an increase of the total flow rate leads to a decrease of the average particle size. More importantly, the average particle size was found to be highly consistent as indicated by a small standard deviation. In particular a high total flow rate of 248 mL/min seems to represent favourable conditions for obtaining consistent average particle sizes.

TABLE 1

|  | Series 1A | Series 1B | Series 1C |
|---|---|---|---|
| Total flow rate [mL/min] | 110 | 176 | 248 |
| n (experiments) | 5 | 10 | 5 |
| Mean z-average [nm] | 202.6 | 184.0 | 154.2 |
| Minimum z-average [nm] | 195.9 | 165.7 | 151.6 |
| Maximum z-average [nm] | 210.6 | 198.5 | 156.3 |
| Standard deviation [nm] | 5.3 | 10.0 | 2.1 |
| Standard deviation [%] | 2.6 | 5.5 | 1.4 |

Example 2

The experiments of this example were conducted to determine the robustness of the PLGA nanoparticle preparation method used in example 1 with respect to the potential PLGA batch-to-batch variability, PLGA providers and polysorbate 20 quality. At a total flow rate of 176 mL/min, series of experiments were conducted as in example 1, except that for series 2A a different PLGA batch was used, for series 2B a PLGA formally having the same specification but obtained from a different provider was used, and for series 2C a different polysorbate 20 quality was used. In result, it was found that the average size of the PLGA nanoparticles was not significantly affected by the changes (see table 2).

TABLE 2

|  | Series 2A | Series 2B | Series 2C |
|---|---|---|---|
| Mean z-average [nm] | 185.4 | 173.6 | 182.3 |

Example 3

The experiments of example 1 were repeated using an apparatus of the same type, design and configuration, and also using the same process parameters (i.e. flow rates). The results confirmed that the preparation of PLGA nanoparticles is highly reproducible such as to enable the validation method according to the invention (see table 3).

TABLE 3

|  | Series 3A | Series 3B | Series 3C |
|---|---|---|---|
| Total flow rate [mL/min] | 110 | 176 | 248 |
| n (experiments) | 10 | 10 | 10 |
| Mean z-average [nm] | 205.4 | 181.0 | 160.6 |
| Minimum z-average [nm] | 192.4 | 163.3 | 148.8 |
| Maximum z-average [nm] | 215.1 | 189.5 | 168.8 |
| Standard deviation [nm] | 8.4 | 3.0 | 2.2 |
| Standard deviation [%] | 4.1 | 1.7 | 1.4 |

Example 4

The experiments of this example were conducted to illustrate the use of the method according to the present disclosure to validate and assess the functioning of an apparatus comprising a jet impingement reactor with another apparatus of the same type, design and configuration. The jet impingement reactor used in this example is different to the reactor used in Example 1, and is reactor described in PCT/EP2022/073361.

Each of the apparatus comprising the jet impingement reactor ('Apparatus 1', 'Apparatus 2') was used at room temperature to repeatedly produce PLGA nanoparticles and determine their average particle size (as z-average) by dynamic light scattering.

A solution of a PLGA having a lactide:glycolide ratio of 75:25, a carboxylic acid end group, and a mean molecular weight of approximately 20 kDa, in acetone having a polymer concentration of 35 mg/mL was used as a first liquid composition, and a solution of polysorbate 20 in deionized water having a surfactant concentration of 0.1 wt. % was used as the second liquid composition according to the present disclosure.

The PLGA solution was injected into the reactor through an inlet having a pinhole nozzle with a diameter of 200 µm, whereas the second inlet through which the aqueous surfactant solution was injected had a pinhole diameter of 300 µm. The surfactant solution was injected into the reactor at a 10 times higher flow rate than the PLGA solution. The mixing of the two liquids lead to the formation of a PLGA nanoparticle dispersion which was discharged from the reactor through an outlet and collected for particle size measurement. The PLGA nanoparticle samples for particle size measurement were collected at the same time point in each experiment. After collection, the samples were diluted 1:10 with deionized sterile filtered water, and then characterized using dynamic light scattering to determine particle size (z-average) and PDI.

Two series of experiments was conducted, in which the total flow rate (sum of both flow rates) was varied, with one set of experiments conducted at a total flow rate of 110 ml/min and the second set of experiments conducted at a total flow rate of 220 ml/min. The results are summarized in Table 4.

TABLE 4

|  | Apparatus 1 | Apparatus 2 | Apparatus 1 | Apparatus 2 |
|---|---|---|---|---|
| Total flow rate [mL/min] | 110 | 110 | 220 | 220 |
| n (experiments) | 5 | 5 | 5 | 5 |
| Mean z-average [nm] | 99.9 | 111.3 | 104.7 | 105.3 |
| Minimum z-average [nm] | 82.1 | 106.6 | 95.3 | 103.1 |
| Maximum z-average [nm] | 108.11 | 111.6 | 111.9 | 107.6 |
| Standard deviation [nm] | 11.4 | 5.9 | 6.3 | 1.9 |

The mean polydispersity index for all experiments was less than 0.25, indicating sufficiently monodisperse particle size distributions. In result, and as shown in Table 4, it was found that through performing the method and using the compositions as described according to the present disclosure, no significant differences in average particle size could be detected between the first apparatus and second apparatus setup, confirming the reproducibility.

The invention claimed is:
1. A method for validating the functioning of an apparatus for producing nanoparticles, said apparatus comprising a static mixing device for mixing two liquid streams, said static mixing device comprising a first fluid inlet, a second fluid inlet, a mixing zone and a fluid outlet, said method comprising the steps of:

(a) providing a first specimen of said apparatus;
(b) providing a first stream of a first liquid composition, wherein the first liquid composition comprises an organic solution of a polymer selected from PLA, PGA, PLGA and combinations thereof;
(c) providing a second stream of a second liquid composition, wherein the second liquid composition is an aqueous solution;
(d) simultaneously injecting the first stream at a first flow rate through the first fluid inlet, and the second stream at a second flow rate through the second fluid inlet into the static mixing device of a first specimen of the apparatus such as to allow the first liquid composition and the second liquid composition to mix in the mixing zone and to form polymer nanoparticles;
(e) measuring the average particle size of the nanoparticles obtained in step (d);
(f) repeating steps (a) to (e) using essentially the same liquid compositions and the same flow rates but a second specimen of the apparatus;
(g) determining whether the difference between the average particle size obtained when step (e) was repeated and the average particle size obtained when step (e) was performed for the first time is larger than a predefined tolerance value; and
(h) if said difference is not larger than the predefined tolerance value, using the second specimen of the apparatus for preparing nanoparticles by mixing two liquid streams that do not comprise the first liquid composition.

2. The method of claim 1, wherein the first and the second specimen of the apparatus have essentially the same design and configuration.

3. The method of claim 2, wherein the second specimen of the apparatus is identical with the first specimen, and wherein the apparatus is, between step (e) when performed for the first time and step (f):
disassembled and reassembled,
cleaned, and/or
used for preparing nanoparticles comprising a biologically active ingredient.

4. The method of claim 3, wherein the apparatus is, between steps (g) and (h), not:
disassembled and reassembled, and/or
used for preparing nanoparticles comprising a biologically active ingredient.

5. The method of claim 1, wherein second specimen of the apparatus is not identical with the first specimen.

6. The method of claim 1, wherein the static mixing device is or comprises a T-piece mixer, a Y-piece mixer, a vortex mixer, a baffle-based static mixer, a microfluidic mixing device, or a jet impingement reactor.

7. The method of claim 6, wherein the static mixing device is a jet impingement reactor, and wherein the mixing zone is a reaction chamber defined by a reactor wall.

8. The method of claim 7, wherein
the first and the second fluid inlet are arranged at opposite positions of the reactor wall on a first central axis of the reaction chamber such as to point at one another, and wherein each of the first and the second fluid inlet comprises a nozzle; and
the fluid outlet is arranged at a position of the reactor wall that is located on a second central axis of said chamber, the second central axis being perpendicular to the first central axis.

9. The method of claim 1, wherein the first liquid composition and the second liquid composition are essentially free of any biologically active ingredient.

10. The method of claim 1, wherein the predefined tolerance value is 20%, or 15%, or 10%, or 5% of the value of the average particle size as measured in step (e) when performing said step for the first time, respectively.

11. The method of claim 1, wherein the first liquid composition is a solution of PLGA in acetone.

12. The method of claim 11, wherein the PLGA has a lactide:glycolide ratio of 75:25, an acidic end group, and a mean molecular weight of approximately 20 kDa.

13. The method of claim 11, wherein the concentration of the PLGA in acetone is in the range from 10 mg/ml to 100 mg/mL, or from 20 mg/mL to 80 mg/mL.

14. The method of claim 1, wherein the second liquid composition comprises a surfactant.

15. The method of claim 14, wherein the surfactant is polysorbate 20, and wherein the concentration of the polysorbate 20 in the second liquid composition is from 0.1 wt. % to 2 wt. %.

16. The method of claim 14, wherein the surfactant is a non-ionic surfactant selected from polysorbates and poloxamers.

17. The method of claim 1, wherein the first liquid composition is a solution of PLGA in acetone, wherein the PLGA has a lactide:glycolide ratio of 75:25, an acidic end group, and a mean molecular weight of approximately 20 kDa and the concentration of PLGA in acetone is in the range of 20 mg/ml to 80 mg/mL, and wherein the second liquid composition is an aqueous solution comprising polysorbate 20, wherein the concentration of polysorbate is from 0.1 wt % to 2 wt %.

* * * * *